US010974076B2

(12) United States Patent
Bowman et al.

(10) Patent No.: US 10,974,076 B2
(45) Date of Patent: Apr. 13, 2021

(54) DYNAMIC THREE-DIMENSIONAL BEAM MODIFICATION FOR RADIATION THERAPY

(71) Applicant: Varian Medical Systems, Inc., Palo Alto, CA (US)

(72) Inventors: Elizabeth Bowman, Palo Alto, CA (US); Roberto Luevano, Aptos, CA (US); Stephen Mohr, Danville, CA (US); Cody Hellstern, Sunnyvale, CA (US); Borislav Djurovic, San Jose, CA (US)

(73) Assignee: Varian Medical Systems, Inc, Palo Alto, CA (US)

( * ) Notice: Subject to any disclaimer, the term of this patent is extended or adjusted under 35 U.S.C. 154(b) by 504 days.

(21) Appl. No.: 15/842,693

(22) Filed: Dec. 14, 2017

(65) Prior Publication Data
US 2018/0161600 A1   Jun. 14, 2018

Related U.S. Application Data

(60) Provisional application No. 62/434,053, filed on Dec. 14, 2016.

(51) Int. Cl.
*A61N 5/10*   (2006.01)
*G21K 1/10*   (2006.01)
*G21K 1/04*   (2006.01)

(52) U.S. Cl.
CPC ........... *A61N 5/1077* (2013.01); *G21K 1/046* (2013.01); *G21K 1/10* (2013.01); *A61N 2005/1095* (2013.01)

(58) Field of Classification Search
CPC .......... A61N 2005/1095; A61N 5/1077; A61N 5/1042; G21K 1/046; G21K 1/10; G21K 1/04
See application file for complete search history.

(56) References Cited

U.S. PATENT DOCUMENTS 6,617,598 B1   9/2003   Matsuda
6,777,700 B2   8/2004   Yanagisawa et al.
6,847,700 B1   1/2005   Mitra et al.
(Continued)

OTHER PUBLICATIONS

Ultrahigh Dose-Rate FLASH Irradiation Increases the Differential Response Between Normal and Tumor Tissue in Mice; Favaudon, et al. Research Article; www.sciencetranslationalmedicine.org; Jul. 16, 2014; vol. 6 Issue 245 pp. 1-9.
(Continued)

*Primary Examiner* — Christine H Matthews

(57) ABSTRACT

A beam modifier shapes the distribution of a dose delivered to a target by a radiation beam emitted from a beam emitter of a radiotherapy device, particularly a beam that delivers a high radiation dose within a single, short period of time (e.g., less than a second). Elements of the beam modifier (e.g., rods) include material that can block or attenuate the beam. The elements can be dynamically and quickly configured to form an opening or transparent area through which a portion of the beam can pass unimpeded and to present different thicknesses of material to block or attenuate other portions of the beam, in this manner shaping the dose distribution at the target while protecting surrounding tissue.

20 Claims, 14 Drawing Sheets

(56) References Cited

U.S. PATENT DOCUMENTS

| | | |
|---|---|---|
| 7,049,613 B2 | 5/2006 | Yanagisawa et al. |
| 7,102,144 B2 | 9/2006 | Matsuda et al. |
| 7,227,161 B2 | 6/2007 | Matsuda et al. |
| 7,268,358 B2 | 9/2007 | Ma et al. |
| 7,285,203 B2 | 10/2007 | Russell et al. |
| 7,397,054 B2 | 7/2008 | Natori et al. |
| 7,449,701 B2 | 11/2008 | Fujimaki et al. |
| 7,456,415 B2 | 11/2008 | Yanagisawa et al. |
| 7,550,752 B2 | 6/2009 | Keppel et al. |
| 7,589,334 B2 | 9/2009 | Hiramoto et al. |
| 7,807,982 B2 | 10/2010 | Nishiuchi et al. |
| 7,825,388 B2 | 11/2010 | Nihongi et al. |
| 7,875,868 B2 | 1/2011 | Moriyama et al. |
| 8,030,627 B2 | 10/2011 | Gentry et al. |
| 8,039,819 B2 | 10/2011 | Faure et al. |
| 8,106,371 B2 | 1/2012 | Fujii et al. |
| 8,129,699 B2 | 3/2012 | Balakin |
| 8,198,607 B2 | 6/2012 | Balakin |
| 8,253,113 B2 | 8/2012 | Nishiuchi et al. |
| 8,263,954 B2 | 9/2012 | Iwata |
| 8,395,131 B2 | 3/2013 | Wu et al. |
| 8,618,521 B2 | 12/2013 | Loo et al. |
| 8,658,991 B2 | 2/2014 | Pu et al. |
| 8,716,663 B2 | 5/2014 | Brusasco et al. |
| 8,754,386 B2 | 6/2014 | Iwata |
| 8,829,476 B2 | 9/2014 | Keppel et al. |
| 8,847,179 B2 | 9/2014 | Fujitaka et al. |
| 9,333,374 B2 | 5/2016 | Iwata |
| 9,855,445 B2 | 1/2018 | Mansfield |
| 2005/0058245 A1 * | 3/2005 | Ein-Gal ................ G21K 1/046 378/65 |
| 2005/0087700 A1 | 4/2005 | Tadokoro et al. |
| 2006/0022152 A1 | 2/2006 | Natori et al. |
| 2006/0163496 A1 | 7/2006 | Hiramoto et al. |
| 2006/0226372 A1 | 10/2006 | Yanagisawa et al. |
| 2007/0034812 A1 | 2/2007 | Ma et al. |
| 2007/0164227 A1 | 7/2007 | Yoshida |
| 2007/0228291 A1 | 10/2007 | Hiramoto et al. |
| 2007/0252093 A1 | 11/2007 | Fujimaki et al. |
| 2008/0067401 A1 | 3/2008 | Harada |
| 2009/0283702 A1 | 11/2009 | Umezawa et al. |
| 2010/0127184 A1 | 5/2010 | Balakin |
| 2010/0301235 A1 | 12/2010 | Bert et al. |
| 2011/0240874 A1 | 10/2011 | Iwata |
| 2012/0126135 A1 | 5/2012 | Illemann et al. |
| 2012/0280150 A1 | 11/2012 | Jongen |
| 2012/0313002 A1 | 12/2012 | Ikeda et al. |
| 2013/0087721 A1 | 4/2013 | Nishio et al. |
| 2013/0231516 A1 | 9/2013 | Loo et al. |
| 2014/0014851 A1 | 1/2014 | Asaba |
| 2014/0091734 A1 | 4/2014 | Gall et al. |
| 2016/0135765 A1 | 5/2016 | Vigdor et al. |

OTHER PUBLICATIONS

Ultrahigh Dose-Rate Flash Irradiation Increases the Differential Response Between Normal and Tumor Tissue in Mice; Favaudon, et al. Supplemental Materials, www.sciencetranslationalmedicine.org/cgi/content/full/6/245/245ra93/DC1 Published Jul. 16, 2014.

Design, Otpimisation and Monte Carlo Simulation of a 3D Range-Modulator for Scanned Particle Therapy; PTCOG 55 Annual Conference; May 22-28, 2016.

* cited by examiner

DYNAMIC THREE-DIMENSIONAL BEAM MODIFICATION FOR RADIATION THERAPY

RELATED U.S. APPLICATION

This application claims priority to U.S. Provisional Patent Application No. 62/434,053, filed Dec. 14, 2016, entitled "Dynamic Three Dimensional Compensator," by E. Bowman et al., and incorporated herein by reference in its entirety.

BACKGROUND

The use of radiation therapy (radiotherapy) to treat cancer is well known. Typically, radiotherapy involves directing a treatment beam of high energy therapeutic radiation (e.g., an electron, photon, ion, or proton beam) into a target or target volume (e.g., a tumor or lesion) in a patient. Before the patient is treated with radiation, a treatment plan specific to the patient is developed. Among other things, the treatment plan includes a dose distribution map and settings for controlling the radiotherapy system in order to achieve that dose distribution.

Multi-leaf collimators (MLCs) are commonly used in radiotherapy systems to shape the treatment beam. Typically, an MLC includes two sets of independently adjustable leaves. The first set of leaves is positioned on one side of the beam's path, and the second set is positioned on the other side of the beam's path. Each leaf is thick enough to either completely block or attenuate a beam of radiation. The leaves can be positioned independently of one another to form an aperture so that the shape of the beam corresponds to the shape of the target. In this manner, the target is exposed to the beam while irradiation of tissue surrounding the target is blocked or reduced.

The MLC can be used to shape the beam topography at each treatment field through dynamic leaf movements. That is, by extending and retracting the leaves during the time period in which the beam is on and irradiating the target, the shape of the beam can be changed to provide the dose distribution prescribed in the treatment plan. In effect, while the beam is on, the dose is painted across the target by moving the leaves to expose each location (area) in the target to the beam for the length of time specified in the treatment plan in order to achieve the prescribed dose at that location.

A recent radiobiology study has demonstrated the effectiveness of delivering an entire, relatively high radiation dose to a target within a single, short period of time (within a fraction of a second, e.g., half a second). This type of treatment is referred to generally herein as FLASH radiation therapy (FLASH RT). Evidence to date suggests that FLASH RT advantageously spares normal, healthy tissue from damage when that tissue is exposed to only a single irradiation for only a very short period of time. A high dose that can be delivered in a short period of time may be referred to herein as a "shot."

With FLASH RT, the dose is delivered so quickly that MLC leaves cannot be used to distribute the dose across the target as described above. The leaves cannot be moved fast enough to change the shape of the beam during a shot.

SUMMARY

Instead of using the multi-leaf collimator (MLC) leaves to shape the beam, a preformed compensator (e.g., for proton therapy) or collimator (e.g., for electron therapy and for photon therapy) milled specifically for the patient can be placed in the beam path before each FLASH shot to shape the topography of the shot. However, this solution has disadvantages. For example, a compensator or collimator must be uniquely formed for each patient. Also, once milled, the compensator or collimator cannot be changed to accommodate, for example, changes in the treatment plan or changes in the patient's position, and also limits the options for changing the angle of the beam emitter (e.g., nozzle or target assembly) or beam delivery system (e.g., gantry).

Embodiments according to the invention overcome the shortcomings associated with using MLC leaves and milled compensators or collimators in FLASH radiotherapy (FLASH RT). Embodiments according to the invention include different dynamic three-dimensional beam modifier designs that can be used to shape the distribution of a dose delivered to a target by a radiation beam emitted from a nozzle or target assembly of a radiotherapy system, particularly a beam that delivers a high radiation dose within a single, short period of time (e.g., less than a second). The beam modifier may be a compensator or a collimator depending on the type of radiation beam. Elements of the beam modifier include material that can block or attenuate the beam. The elements can be dynamically and quickly configured to form an opening or a transparent area through which a portion of the beam can pass unimpeded, and to present different thicknesses of material to completely block other portions of the beam or attenuate other portions of the beam to different degrees, in this manner shaping the dose distribution at the target while protecting surrounding tissue.

In some embodiments, the beam modifier includes groups of opposing rods that are at different angles relative to an incident radiation beam and at different elevations relative to each other. Each of the groups includes multiple layers of rods. The beam modifier can be configured by selectively and independently moving the rods to positions that intersect the beam. Rods can be positioned to create an opening in the beam modifier through which the beam can pass. Rods at different elevations can overlap other rods to attenuate or block portions of the beam outside the opening. For example, to completely block a portion of the beam, a sufficient number of rods can be inserted from different directions to overlap in that portion of the beam. For example, to attenuate a portion of the beam, a number of overlapping rods can be inserted in that portion, where the degree of attenuation is determined by the number of overlapping rods. The rods can be quickly reconfigured between shots.

In other embodiments, the beam modifier includes layers of blocks (shielding blocks) that block or attenuate the beam and other blocks that are transparent to the beam. The beam modifier can be configured by selectively arranging the blocks. Blocks that are transparent to the beam can be stacked to create the equivalent of an opening through the beam modifier. Shielding blocks can be stacked to attenuate or block the beam outside the transparent portion. For example, to completely block a portion of the beam, a sufficient number of shielding blocks can be stacked in that portion of the beam. For example, to attenuate a portion of the beam, a number of shielding blocks can be stacked in that portion, where the degree of attenuation is determined by the number of stacked shielding blocks. The blocks can be quickly rearranged between shots.

In yet other embodiments, the beam modifier includes columns (channels) that can be filled to different levels with liquid metal that can block or attenuate the beam. The beam modifier can be configured by selectively adding or removing liquid metal from the channels. The equivalent of an opening through the beam modifier can be formed by removing liquid metal from some of the channels. Other channels can be partially filled to attenuate the beam or filled to the level necessary to block the beam. For example, to completely block a portion of the beam, a sufficient amount of liquid metal is added to the channels in that portion of the beam. For example, to attenuate a portion of the beam, less liquid metal is included in the channels in that portion, where the degree of attenuation is determined by the amount of liquid metal in the channels. The amount of liquid metal in each channel can be quickly changed between shots.

Embodiments according to the invention can thus be described as dynamic three-dimensional beam modifiers because they can be configured and reconfigured in three dimensions—across the path of the beam (two dimensions) and in the direction of the beam.

In summary, embodiments according to the invention reduce setup times between dose deliveries, thereby shortening the treatment time and therefore also shortening the total amount of time that the patient needs to remain in position while the treatments are completed. Also, the patient does not need to be moved while reconfiguring the beam modifier, which improves the repeatability and accuracy of the dosage distribution delivered to the target. In addition, embodiments according to the invention provide greater flexibility with respect to patient position, beam delivery system (e.g., gantry) angles, and beam emitter (e.g., nozzle or target assembly) angles, and thus increase the number of treatment options.

Significantly, embodiments according to the invention can be used to control dose distribution during FLASH RT. In particular, the dose distribution of each single FLASH shot can be controlled. Even though a shot may last less than a second, the desired dose distribution can be delivered across a target during the shot. In general, embodiments according to the invention remove time as a variable when distributing doses to the target.

These and other objects and advantages of embodiments according to the present invention will be recognized by one skilled in the art after having read the following detailed description, which are illustrated in the various drawing figures.

This summary is provided to introduce a selection of concepts in a simplified form that is further described below in the detailed description that follows. This summary is not intended to identify key features or essential features of the claimed subject matter, nor is it intended to be used to limit the scope of the claimed subject matter.

BRIEF DESCRIPTION OF DRAWINGS

The accompanying drawings, which are incorporated in and form a part of this specification and in which like numerals depict like elements, illustrate embodiments of the present disclosure and, together with the detailed description, serve to explain the principles of the disclosure.

DETAILED DESCRIPTION

Reference will now be made in detail to the various embodiments of the present disclosure, examples of which are illustrated in the accompanying drawings. While described in conjunction with these embodiments, it will be understood that they are not intended to limit the disclosure to these embodiments. On the contrary, the disclosure is intended to cover alternatives, modifications and equivalents, which may be included within the spirit and scope of the disclosure as defined by the appended claims. Furthermore, in the following detailed description of the present disclosure, numerous specific details are set forth in order to provide a thorough understanding of the present disclosure. However, it will be understood that the present disclosure may be practiced without these specific details. In other instances, well-known methods, procedures, components, and circuits have not been described in detail so as not to unnecessarily obscure aspects of the present disclosure.

Portions of the detailed description that follows are presented and discussed in terms of a method. Although steps and sequencing thereof are disclosed in figures herein (e.g., FIG. 17) describing the operations of this method, such steps and sequencing are exemplary. Embodiments are well suited to performing various other steps or variations of the steps recited in the flowchart of the figure herein, and in a sequence other than that depicted and described herein.

Figure 1:
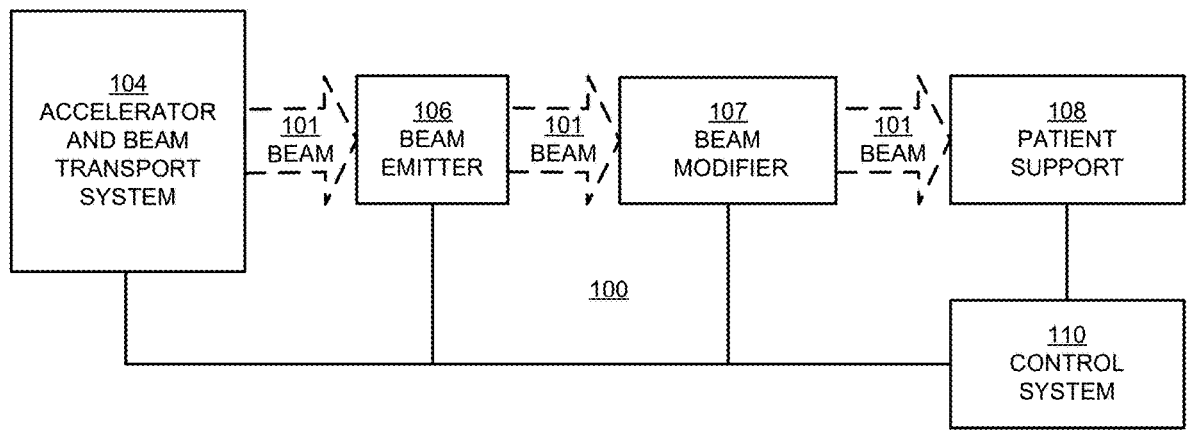
FIG. 1 is a block diagram showing selected components of a radiation treatment (radiotherapy) system upon which embodiments according to the present invention can be implemented.

FIG. 1 is a block diagram showing selected components of a radiation treatment (radiotherapy) system 100 upon which embodiments according to the present invention can be implemented. In the example of FIG. 1, the system 100 includes an accelerator and beam transport system 104 that generates and/or accelerates and/or delivers a radiation beam 101. In embodiments according to the invention, the system 100 can be a system that can generate and deliver proton beams, electron beams, neutron beams, photon beams, ion beams, or atomic nuclei beams (e.g., beams using elements such as carbon, helium, or lithium). The operations and parameters of the accelerator and beam transport system 104 are controlled so that the intensity, energy, size, and/or shape of the beam are dynamically modulated or controlled during treatment of a patient according to a radiation treatment plan.

For FLASH radiotherapy (RT), the accelerator and beam transport system 104 can generate beams that can deliver at least four grays (Gy) in less than one second, and may deliver as much as 20 Gy or 50 Gy or more in less than one second.

The beam emitter 106 is used to aim the beam toward various locations (a target) within a patient supported on the patient support device 108 (e.g., a chair, couch, or table) in a treatment room. The beam emitter 106 may be a nozzle or a target assembly depending on the type of beam. For example, a nozzle is used for proton applications, and a target assembly is used for electron or photon applications. A target may be an organ, a portion of an organ (e.g., a volume or region within the organ), a tumor, diseased tissue, or a patient outline.

The beam emitter 106 may be mounted on or may be a part of a beam delivery system 202 (FIG. 2; e.g., a gantry) that can be moved relative to the patient support device 108, which may also be moveable. In embodiments, the accelerator and beam transport system 104 is also mounted on or is a part of the beam delivery system 202; in another embodiment, the accelerator and beam transport system is separate from (but in communication with) the beam delivery system.

Continuing with reference to FIG. 1, a beam modifier 107 is situated between the beam emitter 106 and the patient support 108. That is, the beam modifier 107 is positioned outside the beam emitter 106, between the beam emitter and the target. The beam modifier 107 may be a compensator or a collimator depending on the type of radiation beam. For example, a compensator is used for proton applications, and a collimator is used for electron or photon applications. The beam modifier 107 and its function(s) are described further below. The beam 101 is thus generated by the accelerator and beam transport system 104 and is emitted from the beam emitter 106 to and through the beam modifier 107, then to the target.

Figure 18:
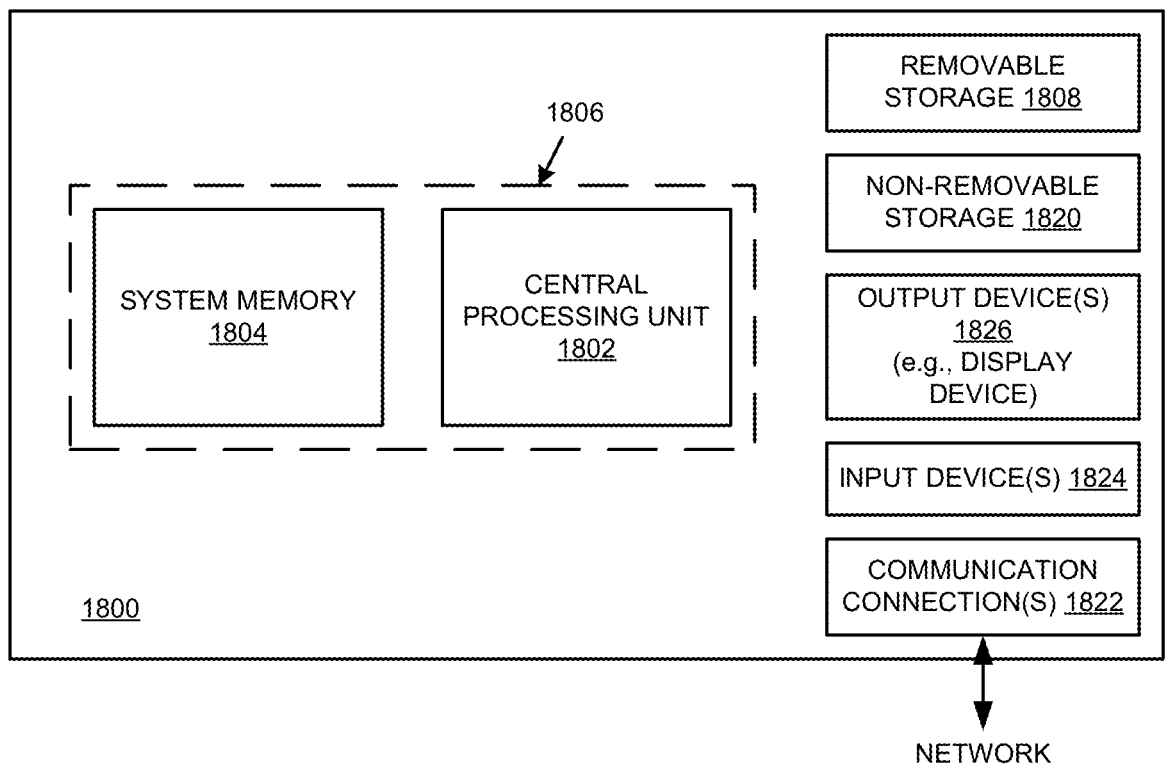
FIG. 18 shows a block diagram of an example of a computing system with which the embodiments described herein may be implemented.

The control system 110 receives and implements a prescribed treatment plan. In embodiments, the control system 110 includes a computing system having a processor, memory, an input device (e.g., a keyboard), and perhaps a display. The system 1800 of FIG. 18 is an example of a platform for the control system 110. The control system 110 can receive data regarding operation of the radiotherapy system 100. The control system 110 can control parameters of the accelerator and beam transport system 104, beam emitter 106, beam modifier 107, beam delivery system 202 (FIG. 2) and patient support device 108, including parameters such as the energy, intensity, size, and/or shape of the beam, direction of the beam emitter, configuration of the beam modifier, and position of the patient support device (and the patient) relative to the beam emitter, according to data the control system 110 receives and according to the radiation treatment plan.

Figure 2:
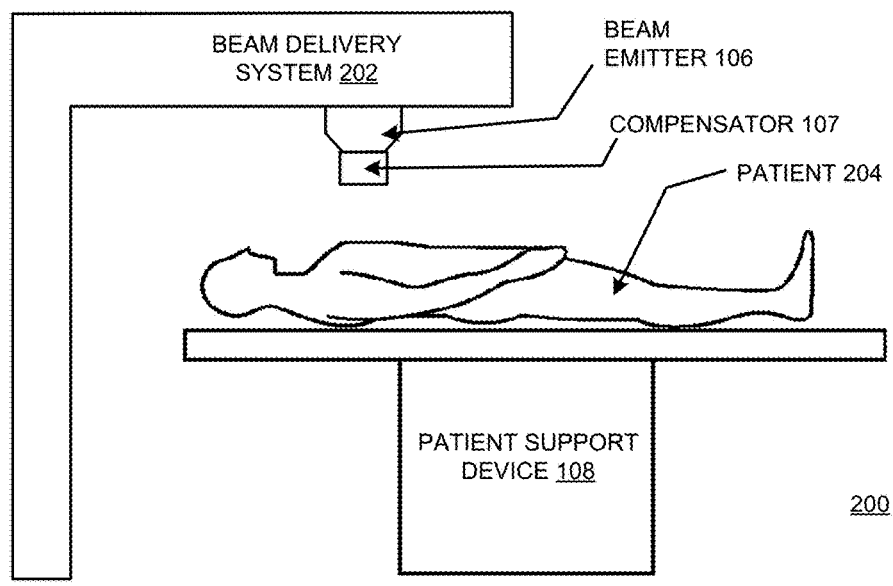
FIG. 2 illustrates elements of a radiotherapy system in embodiments according to the invention.

FIG. 2 illustrates elements of a radiotherapy system 200 for treating a patient 204 in embodiments according to the invention. The system 200 is an example of an implementation of the radiotherapy system 100 of FIG. 1. In embodiments, the beam delivery system 202 and beam emitter 106 can be moved up and down the length of the patient 204 and/or around the patient, and the beam delivery system and beam emitter can move independently of one another. In embodiments, the patient support device 108 can be moved to different positions relative to the beam delivery system 202 and beam emitter 106, rotated about its longitudinal axis, rotated about a central (normal) axis, and/or tilted back and forth about a transverse axis. While the patient 204 is supine in the example of FIG. 2, the invention is not so limited. For example, the patient 204 can instead be seated in a chair.

As noted, the radiotherapy system 200 also includes a beam modifier 107 that is located outside the beam emitter 106. The beam modifier 107 can be attached to the beam emitter 106, it can be incorporated into the beam emitter, or it can be held in place downstream of the beam emitter in some other manner. In general, the beam modifier 107 can be moved in concert with the beam emitter 106 so that a radiation beam emitted from the beam emitter will pass through the beam modifier before the beam reaches its target. This provides greater flexibility with respect to patient position and beam delivery system/beam emitter angles and thus increases the number of treatment options.

As will be explained further below, the beam modifier 107 can be configured and reconfigured depending, for example, on the treatment plan, in order to achieve the dose distribution prescribed in the treatment plan. In embodiments, the beam modifier 107 can be configured and reconfigured while in place in the radiotherapy system 200. In other embodiments, the beam modifier 107 can be removed from the radiotherapy system 200, reconfigured, and then replaced into the system.

Embodiments according to the invention include different dynamic three-dimensional beam modifier designs that can be used to shape the distribution of a dose delivered to a target by a radiation beam emitted from a beam emitter of a radiotherapy system, particularly a beam that delivers a high radiation dose within a single, short period of time (e.g., less than a second). The beam modifier designs are more specifically described below.

Rod-Based Beam Modifier

Figure 3:
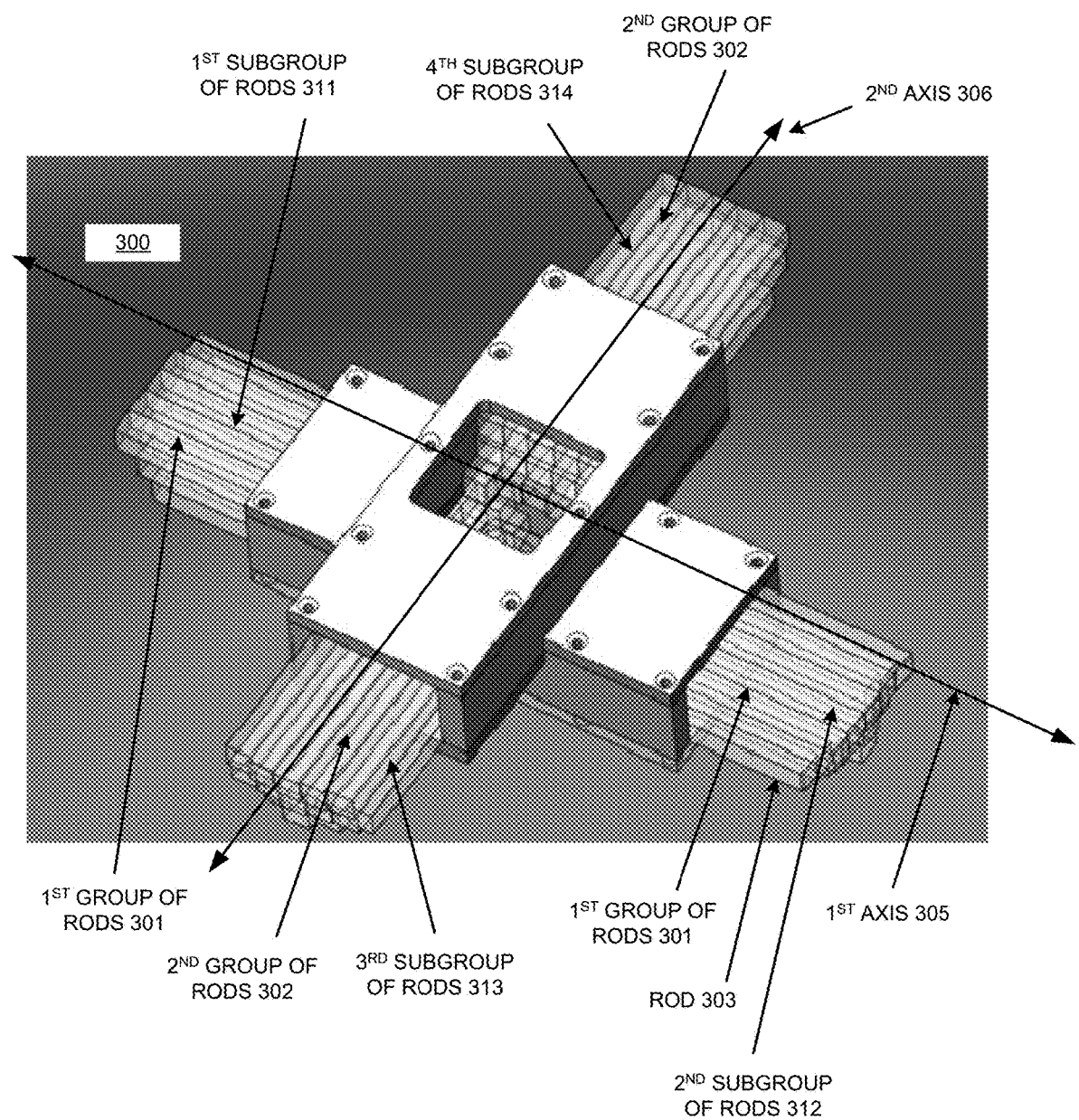
FIG. 3 illustrates a beam modifier in embodiments according to the invention.

FIG. 3 illustrates a beam modifier 300 in embodiments according to the invention. The beam modifier 300 is an example of the beam modifier 107 of FIGS. 1 and 2. The beam modifier 300 includes a number of individual rods exemplified by the rod 303. In embodiments, each rod is solid along its entire length; however, the invention is not so limited. For example, portions of the rods that will not be inserted into the path of an incident radiation beam may not be solid.

In the FIG. 3 embodiments, the beam modifier 300 includes a first group 301 of the rods and a second group 302 of the rods. Each rod can be moved (extended and retracted) independently of the other rods, and the distance each rod is moved can be independently controlled. More specifically, the first group 301 includes a number of opposing rods that can each move independently along a respective axis of travel that is parallel to a first axis 305, and the second group 302 also includes a number of opposing rods that can each move independently along a respective axis of travel that is parallel to a second axis 306. Each rod can be moved any distance; that is, a rod may be all the way inserted or all the way withdrawn or at any point between these extremes. Opposing rods are rods that are parallel to the same axis and that have ends that face each other; the end of a rod is the surface of the rod that intersects the longitudinal axis of the rod (the rod's axis of travel).

Each of the rods in the beam modifier 300 can include material that completely blocks a radiation beam or material that attenuates a radiation beam. As mentioned above, the beam may be, for example, a proton beam, electron beam, neutron beam, photon beam, ion beam, or atomic nuclei beam. The rod material can be, for example, a high density metal such as, but not limited to, tungsten, tungsten alloys, tantalum, tantalum alloys, lead, lead alloys, brass alloys, or copper alloys. For proton beams, the rod material can be graphite, for example. In embodiments, the same material is used along the entire length of each rod. However, the invention is not so limited. For example, a different material may be used in the portions of the rods that will not be inserted into the path of an incident radiation beam. In embodiments, as described below in conjunction with FIG. 7, some rods may include a portion that is transparent to the beam.

Continuing with reference to FIG. 3, the first axis 305 and the second axis 306 are not parallel to each other. In the example of FIG. 3, the first axis 305 and the second axis 306 are orthogonal to each other; however the invention is not so limited. In embodiments, the first group 301 of rods and/or the second group 302 of rods can be moved to change the angle between the first axis 305 and the second axis 306. More specifically, the first group 301 of rods and/or the second group 302 of rods can be rotated collectively relative to each other, so that the angle between them (and between the axes 305 and 306) can be adjusted to facilitate implementation of the treatment plan.

Figure 4:
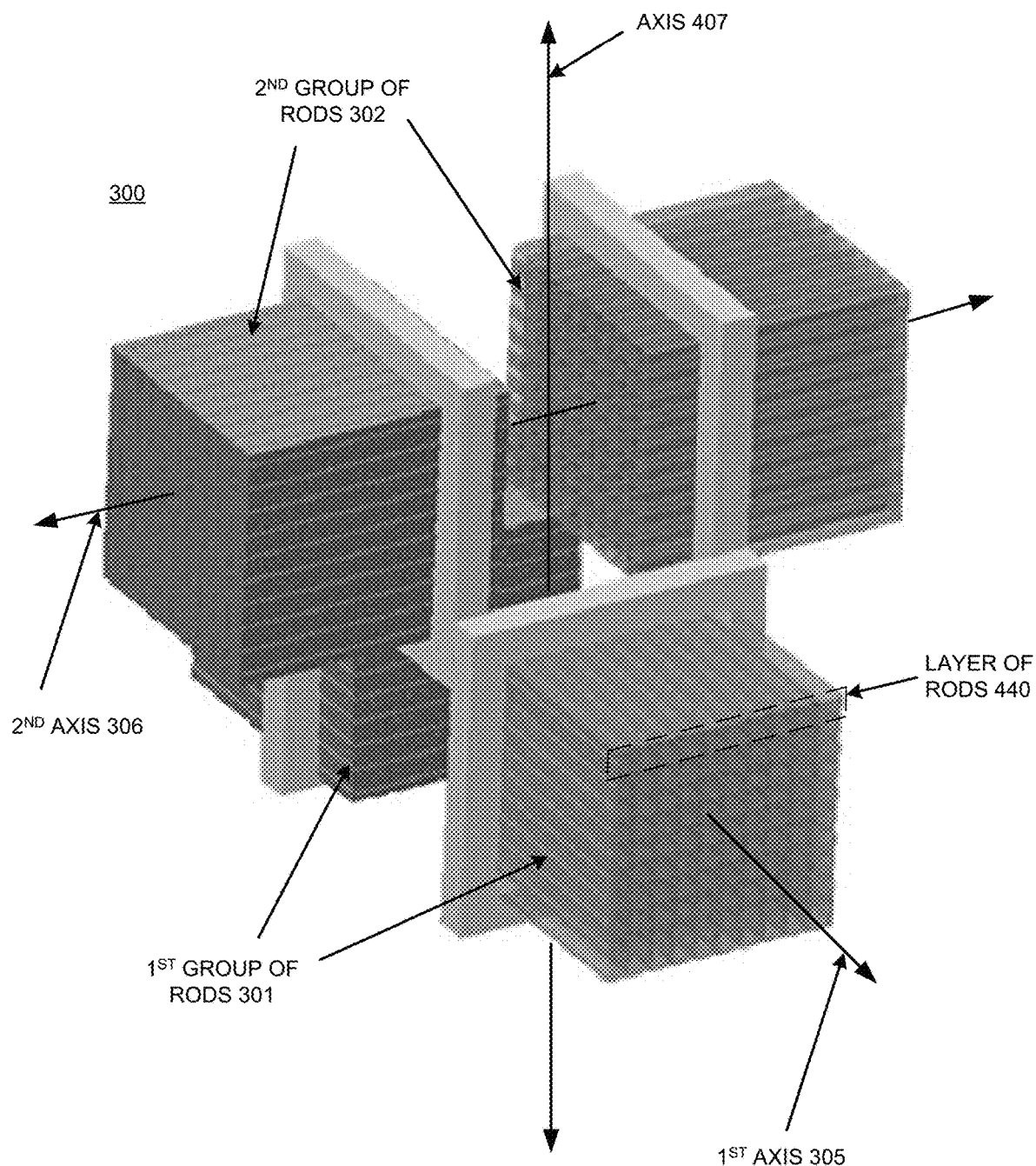
FIG. 4 illustrates another view of a beam modifier like that of FIG. 3 in embodiments according to the invention.

The first group 301 of rods includes a first subgroup 311 of rods disposed in multiple first layers and a second subgroup 312 of opposing rods disposed in multiple second layers (e.g., the layer 440 of FIG. 4). The second group 302 of rods includes a third subgroup 313 of rods disposed in multiple third layers and a fourth subgroup 314 of opposing rods disposed in multiple fourth layers. Each of the first, second, third, and fourth layers includes multiple rods. In an embodiment, there are ten layers per subgroup and ten rods per layer (that is, ten rows and ten columns of rods per subgroup). In an embodiment, the height of a rod is one centimeter, and the width is also one centimeter. The rods can be of any practical length, width, and height.

In embodiments, the first subgroup 311 and the second subgroup 312 are aligned, and each of the rods in one of these subgroups is aligned with a corresponding rod in the other of these subgroups. Similarly, in embodiments, the third subgroup 313 and the fourth subgroup 314 are aligned, and each of the rods in one of these subgroups is aligned with a corresponding rod in the other of these subgroups. In other words, for example, when a rod in the subgroup 311 is moved toward the center of the beam modifier 300, and the corresponding opposing rod in the subgroup 312 is moved toward the center of the beam modifier, then those rods will both lie on the same axis and their ends will touch if the rods are moved to their fullest extent. In these embodiments, the number of rods in each subgroup is the same. However, the invention is not so limited. For example, in some embodiments, the number of rods in the subgroups 311 and 312 is the same, and the number of rods in the subgroups 313 and 314 is the same but is different from the number of rods in the subgroups 311 and 312.

FIG. 4 illustrates another view of the beam modifier 300 in embodiments according to the invention. As can be seen in the figure, the first and second groups of rods 301 and 302 are at different elevations in the direction parallel to the axis 407 (which is orthogonal to the axes 305 and 306). That is, one of the subgroups is closer to the source of the radiation beam 101 (FIG. 1) than the other. The axis 407 corresponds to the axis of the incident radiation beam 101. Accordingly, if rods in the subgroup 311 and/or subgroup 312 are moved far enough toward the beam axis 407 (e.g., into the radiation beam) and rods in the subgroup 313 and/or the subgroup 314 are also moved far enough toward the beam axis, then rods in the first and second groups 301 and 302 will overlap and can be used to block and/or attenuate some portions of the radiation beam.

Figure 5A:
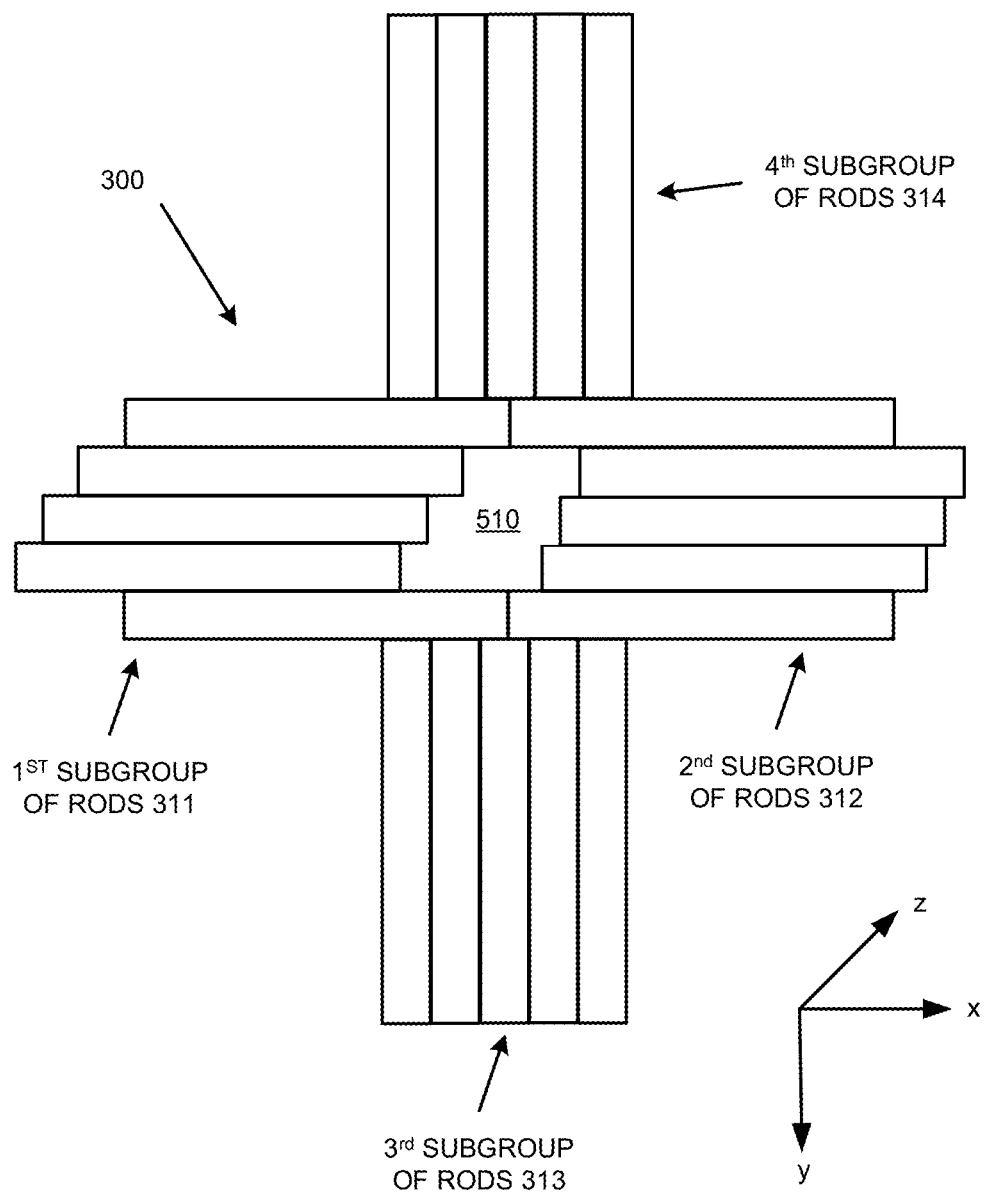
FIG. 5A illustrates another view of a beam modifier like that of FIG. 3 in embodiments according to the invention.

FIG. 5A illustrates a top-down view of the beam modifier 300 in embodiments according to the invention. Only a single layer (e.g., the top layer) of rods is inserted in the example of FIG. 5A. In this example, some of the rods in the subgroups 311 and 312 are only partially inserted toward the center of the beam modifier, and some of the rods in the subgroups 311 and 312 are fully inserted until they are in contact with opposing rods. The rods in the subgroups 313 and 314 are not inserted in the example of FIG. 5A; however, they could be inserted various distances. In FIG. 5A, while only five rods per subgroup are illustrated, the invention is not so limited.

The gaps between the rods form an opening 510. The shape of the opening 510 depends on how many of the rods are inserted and how far they are inserted.

As shown in the example of FIG. 4 above, there can be multiple layers of rods per subgroup. Thus, in the example of FIG. 5A, there may be layers of rods between the layer of rods of the first and second subgroups 311 and 312 and the layer of rods of the third and fourth subgroups 313 and 314.

More specifically, as mentioned above, the subgroups 311, 312, 313, and 314 include multiple layers of rods, the rods can be individually moved different distances, and the rods in the subgroups 311 and 312 can overlap the rods in the subgroups 313 and 314 (and vice versa) depending on how far they are moved. In an embodiment, there are ten layers per subgroup. Thus, depending on how the rods in the beam modifier 300 are configured, the shape of the opening 510 can be different at each layer of the beam modifier. Also, the thickness of the material around the opening 510, measured in the z-direction of FIG. 5A (into the page), can be varied in the x-direction and in the y-direction of FIG. 5A depending on the number of rods that are inserted.

Figure 5B:
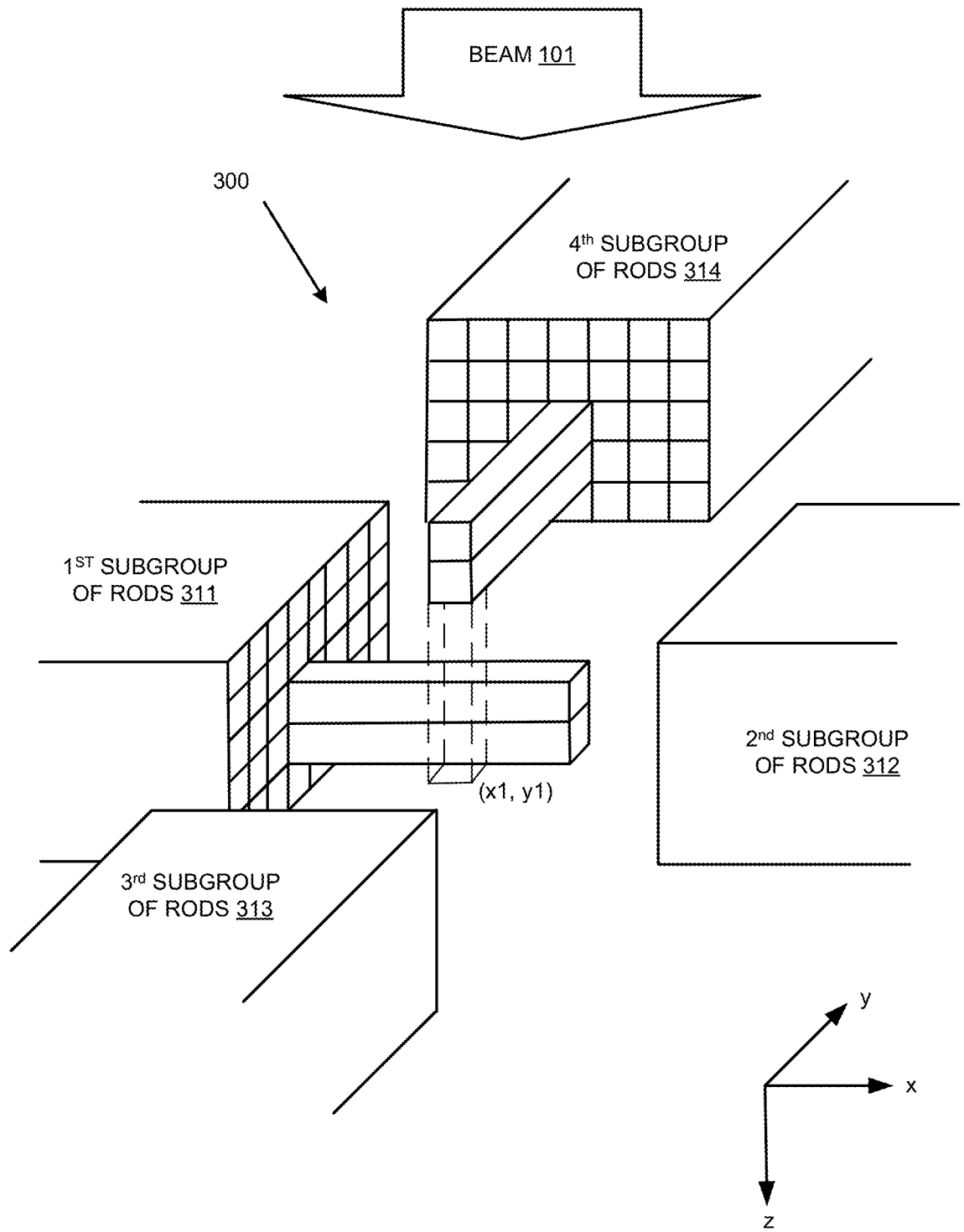
FIG. 5B illustrates overlapping rods in a beam modifier like that of FIG. 3 in embodiments according to the invention.

This is illustrated in FIG. 5B. As described above, the third and fourth subgroups of rods 313 and 314 are at a higher elevation (closer to the source of the beam 101) than the first and second subgroups of rods 311 and 312. At an areal location (x1,y1) in the beam 101, two rods (e.g., adjacent rods) from two layers of the subgroup 311 may be inserted and two rods (e.g., adjacent rods) from two layers of the subgroup 313 may be inserted so that the rods from each subgroup overlap in the beam, in which case the material in the z-direction of FIG. 5B will be four rods thick at the first location. In effect, the four overlapping rods cast a shadow on the target corresponding to the location (x1,y1) where the rods intersect the beam 101, where the depth of the shadow (the amount of blockage or attenuation) depends on whether the rods attenuate the beam or completely block the beam at that location. As mentioned above, there are multiple rows and columns (layers) of rods in each subgroup. Accordingly, there are many possible arrangements of overlapping rods that can be formed in the path of the beam 101, so that each area of the beam can be attenuated or blocked at the same time to achieve a desired dose distribution.

In operation, a radiation beam enters the beam modifier 300 in the z-direction of FIG. 5A and will pass unimpeded through the opening 510. As mentioned above, each of the rods in the beam modifier 300 can include material that completely blocks the beam or material that attenuates the beam. Accordingly, as just described above, different numbers and different lengths of rods can be independently inserted from different directions, layer by layer, to shape the opening 510 and to block portions of the beam completely and/or attenuate portions of the beam by different amounts outside the opening. The overlapping of rods at multiple elevations within the beam creates the desired dosage gradient. The amount of attenuation in a portion of the beam depends on the number of overlapping rods that portion of the beam passes through. In this manner, the beam can be shaped by the beam modifier 300, meaning that the beam modifier both shapes the area of the target covered by the beam and shapes the intensity of the beam that reaches that area, and hence shapes the dose distribution across that area.

Figure 6:
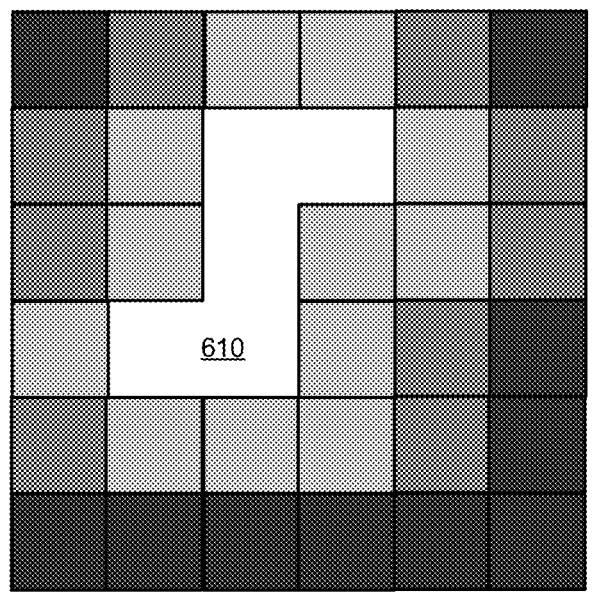
FIG. 6 illustrates beam intensity (dose distribution) achieved using a beam modifier in embodiments according to the invention.

This is represented in FIG. 6, which illustrates the relative intensity of the beam 101 (FIG. 1) after the beam has passed through the beam modifier 300 of FIG. 3, where the beam modifier has been configured to form an opening 610 and has also been configured with overlapping rods that attenuate portions of the beam to different degrees and overlapping rods that completely block portions of the beam. In FIG. 6, the unshaded areas indicate areas where the beam passed through the opening 610 in the beam modifier 300. Lighter-shaded areas indicate areas where the beam was attenuated by the beam modifier 300 and/or areas that are within the beam penumbra. Darker-shaded areas indicate areas where the beam was further attenuated, and the darkest areas indicate areas where the beam was completely blocked. FIG. 6 thus also represents the dose distribution across the target, where the unshaded areas indicate areas that receive the highest dose, and so on.

The beam can be a FLASH shot—a beam that delivers an entire, relatively high radiation dose to the target within a single, short period of time (within a fraction of a second, e.g., half a second). Thus, the beam modifier 300 can control the dose distribution of a FLASH shot. After the shot is delivered, the beam modifier 300 can be rapidly reconfigured by moving rods from their current positions to new positions as needed to change the shape of the opening 510 and/or to change which portions of the beam are to be blocked or attenuated and the amount of attenuation. In embodiments, the beam modifier 300 is remotely configured using the control system 110 of FIG. 1. Once reconfigured, another shot can be delivered. This process can be repeated until the treatments prescribed by the treatment plan are delivered. Specifically, this process is repeated until the prescribed dose distribution across and through the target is achieved.

The beam modifier 300 thus reduces setup time between treatments/shots, which shortens the treatment time and therefore also shortens the total amount of time that the patient needs to be in place on the patient support 108 (FIG. 1). The patient does not need to be moved while the beam modifier 300 is reconfigured, which improves the repeatability and accuracy of the dose distribution delivered to the target.

Figure 7:
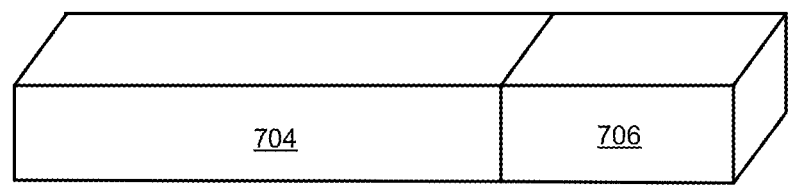
FIG. 7 illustrates a partially transparent rod in a beam modifier like that of FIG. 3 in embodiments according to the invention.

In embodiments, some of the rods in the beam modifier 300 have a portion or volume that is transparent to the radiation beam. FIG. 7 illustrates a partially transparent rod 702 that includes a transparent portion 704 and a portion 706 that blocks or attenuates the beam, in embodiments according to the invention. There may be multiple partially transparent rods in each of the subgroups 311, 312, 313, and 314 of FIG. 3. The length of the transparent portion 704 may or may not be the same in each of the partially transparent rods. Partially transparent rods like the rod 702 can be used, for example, to form a region in the opening 510 that blocks or attenuates the beam.

Figure 8:
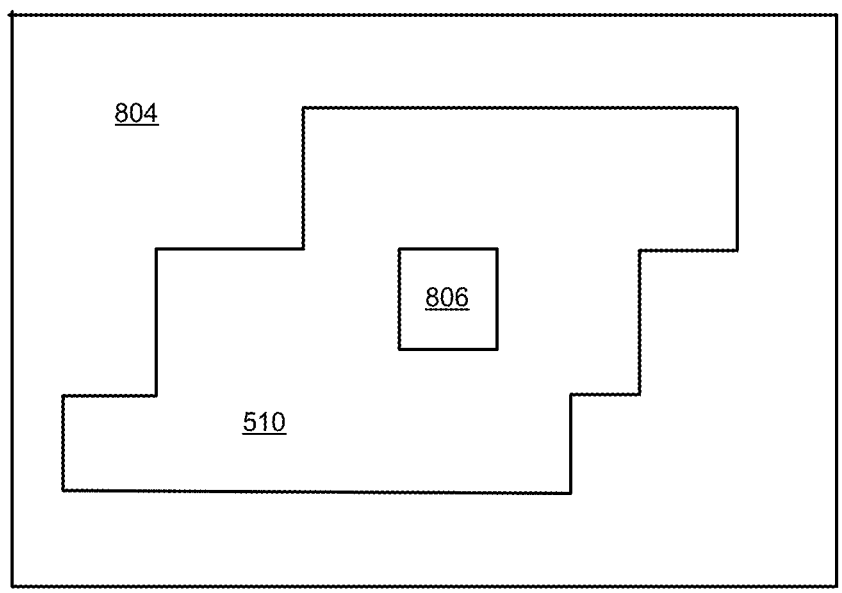
FIG. 8 illustrates an opening in a beam modifier like that of FIG. 3 in embodiments according to the invention.

This is illustrated in FIG. 8, which shows the opening 510 formed by a layer of rods as described above. In the example of FIG. 8, a layer of partially transparent rods 702 (FIG. 7) is inserted as part of or under the layer of rods that form the opening 510. In this manner, the beam is blocked or attenuated in the areas 804 around the perimeter of the opening 510, and is also blocked or attenuated in the area 806 within the opening 510.

Figure 9A:
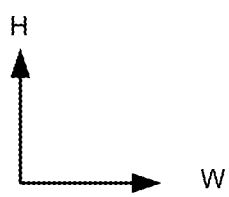
FIGS. 9A, 9B, and 9C illustrate examples of cross-sectional shapes of rods in a beam modifier like that of FIG. 3 in embodiments according to the invention.
Figure 9A:
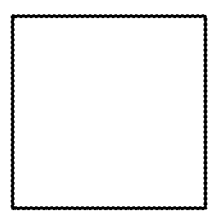
Figure 9B:
Figure 9C:
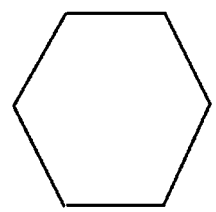

FIGS. 9A, 9B, and 9C illustrate examples of cross-sectional shapes of the rods in the beam modifier 300 of FIG. 3. In an embodiment, the height H of a rod is one centimeter, and the width W is also one centimeter. In the example of FIG. 9A, the cross-section is squarish; that is, the height and width of a rod are equal. In the example of FIG. 9B, the cross-section is rectangular; that is, the height is less than the width. The beam modifier 300 can include a combination of both squarish and rectangular rods. For example, the beam modifier can include one or more layers of squarish rods and one or more layers of rectangular rods. Rods with squarish or rectangular cross-sections are advantageous because they can provide better control over the size of the penumbra and greater flexibility in how they can be configured. In the example of FIG. 9C, the cross-section is hexagonal. Other cross-sectional shapes can be utilized.

Figure 10A:
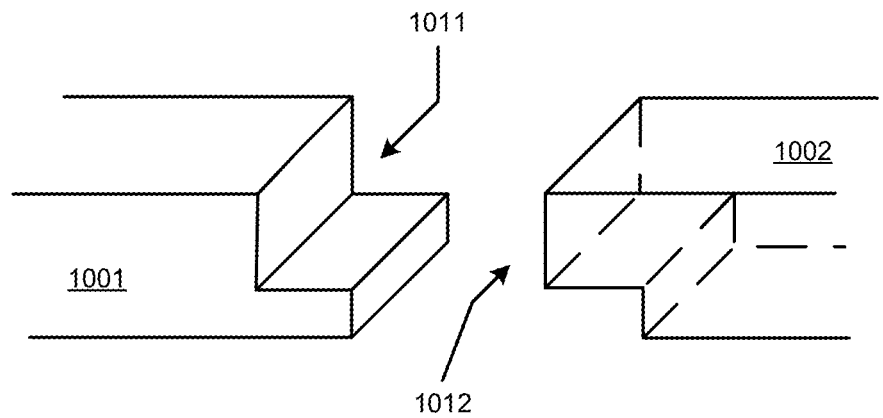
FIG. 10A illustrates the ends of a pair of opposing rods of a beam modifier like that of FIG. 3 in embodiments according to the invention.

FIG. 10A illustrates the ends of a pair of opposing rods 1001 and 1002 of the beam modifier 300 (FIG. 3) in embodiments according to the invention. For instance, the rod 1001 may be in the subgroup 311, and the rod 1002 may be in the subgroup 312. In general, the respective ends 1011 and 1012 of the opposing rods 1001 and 1002 are complementary in shape, allowing the two ends to fit against each other when the rods are brought into contact. The complementary shape of the ends precludes or reduces the amount of radiation leakage between opposing rod end pairs (e.g., between the two rods 1001 and 1002) when the rods are brought into contact with each other in the beam path.

In the example of FIG. 10A, the ends 1011 and 1012 are flat but have step-like surfaces, in which the end 1011 is indented where the end 1012 protrudes in complementary fashion, and vice versa. However, the invention is not so limited. For example, the flat surfaces of the ends 1011 and 1012 can instead be rounded. For example, one of the ends can have a concave surface or surfaces, and the other end can have a complementary convex surface or surfaces.

Figure 10B:
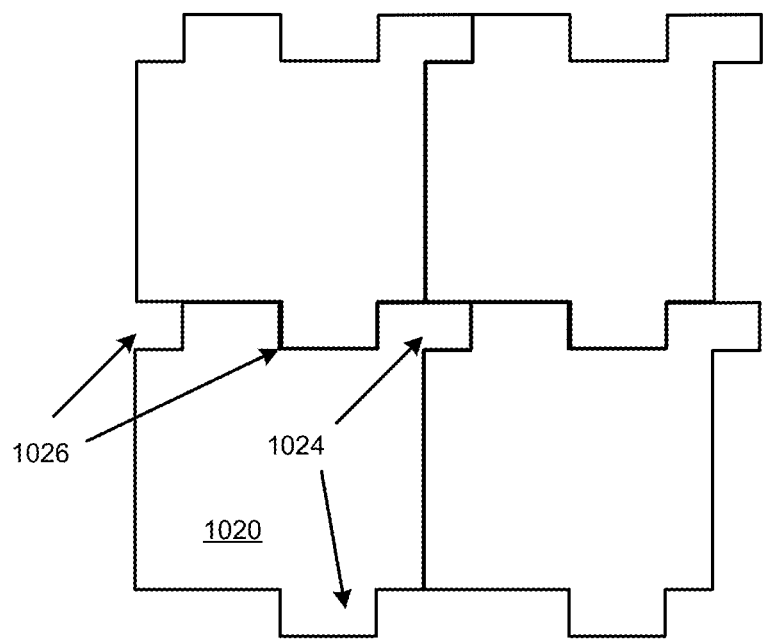
FIG. 10B illustrates cross-sections of rods of a beam modifier like that of FIG. 3 in embodiments according to the invention.

In the examples presented in some of the above figures, the surfaces of the sides of the rods are flat. However, in some embodiments, the surfaces of the sides of the rods are not flat, as shown in the example of FIG. 10B. FIG. 10B is a cross-sectional view showing ends of rods in the beam modifier 300. In the example of FIG. 10B, the rods include protrusions 1024 and indentations 1026 along their lengths (their tops, bottoms, and sides). For instance, the positions of the indentations in the rod 1020 correspond to the positions of the protrusions in the adjacent rods, and vice versa, so that the protrusions fit into the indentations. This type of interlocking rod structure keeps the rods in proper alignment as the rods are moved back-and-forth along their axes of travel. Thus, the rods in the beam modifier 300 can support each other and, therefore, a channel surrounding each rod is not needed. Also, when the rods are inserted into the beam path, the non-flat surfaces preclude or reduce the amount of leakage of radiation through the gaps between the moveable rods.

Figure 11:
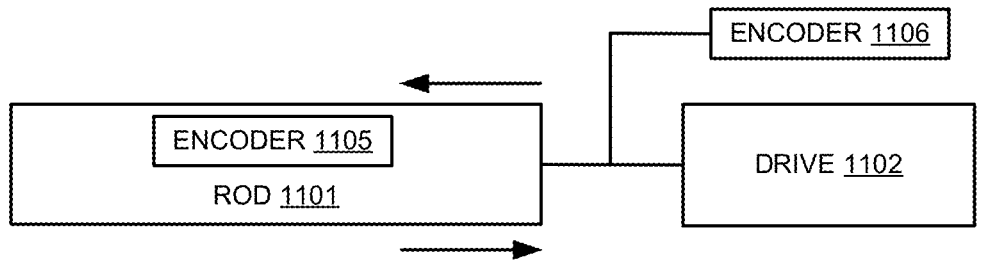
FIG. 11 illustrates a side view of a rod connected to a drive in a beam modifier like that of FIG. 3 in embodiments according to the invention.

FIG. 11 illustrates a side view of a rod 1101 connected to a drive 1102 in the beam modifier 300 in embodiments according to the invention. In embodiments, each rod in the beam modifier 300 is driven by its own drive 1102. For example, there is a motor per rod. The drives also help hold the rods in place and maintain their alignment. In embodiments, a primary encoder 1105 (e.g., a linear encoder) on each drive 1102 provides an indication that the rod 1101 is properly positioned, and a secondary encoder 1106 (e.g., another linear encoder) mounted on a printed circuit board adjacent to the rod 1101 verifies that the rod is properly positioned. Thus, each rod possesses redundant feedback to ensure its location in the radiation field to comply with applicable safety standards.

Block-Based Beam Modifier

Figure 12:
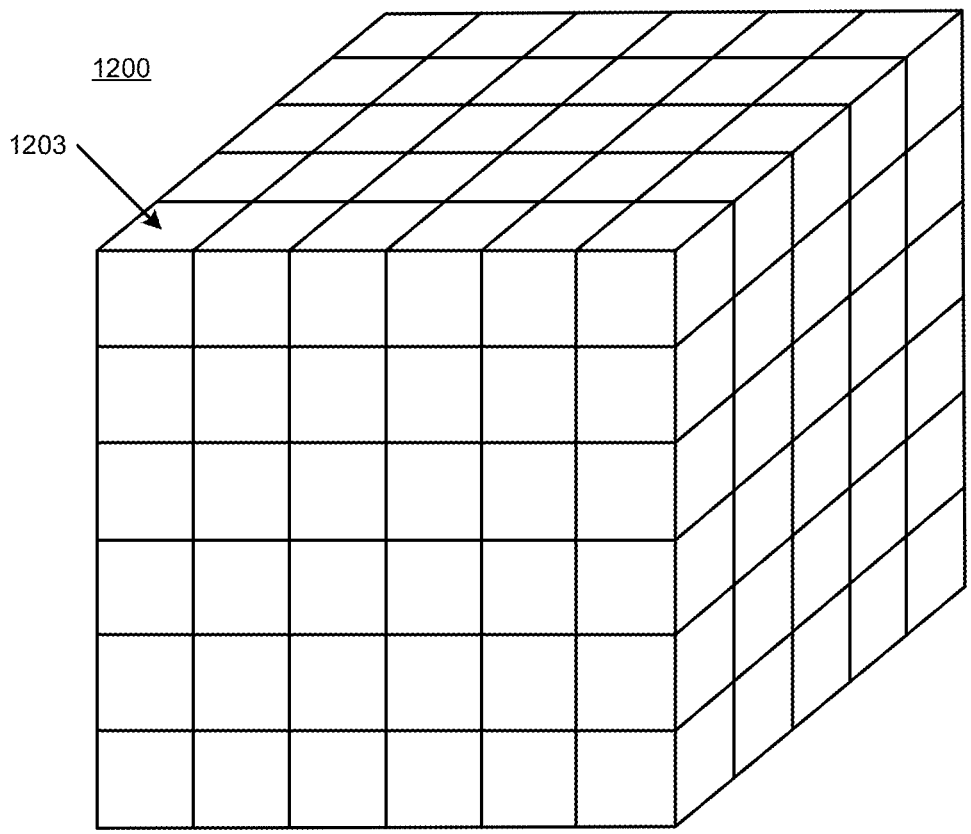
FIG. 12 illustrates a beam modifier in other embodiments according to the invention.

FIG. 12 illustrates a beam modifier 1200 in embodiments according to the invention. The beam modifier 1200 is an example of the beam modifier 107 of FIGS. 1 and 2. The beam modifier 1200 includes a number of individual blocks exemplified by the block 1203. Each block in the beam modifier 1200 is free-standing; that is, the blocks are not connected to each other when in place in the beam modifier 1200, but are stacked on top of and/or side-by-side with other blocks. The blocks are held in place by a container (not shown) that is transparent to the radiation beam 101 (FIG. 1). However, in embodiments, each block can include a mechanism that allows it to be affixed to an adjacent block. In embodiments, the container is open at the top, but a cover can be used to close that opening.

In an embodiment, the blocks in the beam modifier 1200 are arranged in ten rows, ten columns, and ten layers (e.g., a ten-by-ten-by-ten cube of blocks). In an embodiment, each block is cubic. In an embodiment, each block is one cubic centimeter in size.

The invention is not limited to all blocks being the same size or shape. For example, one layer may include blocks of a different size then an adjacent layer, so that the edges of the blocks in the first layer are offset from the edges of the blocks in the adjacent layer. For example, one layer may include cubic blocks and an adjacent layer may include rectangular prisms (rectangular cuboids), or each layer may include a combination of cubic blocks and rectangular prisms. As such, the edges of the blocks in one layer would be offset from the edges of the blocks in the adjacent layer. In this manner, leakage of radiation between blocks is precluded or reduced.

Figure 13:
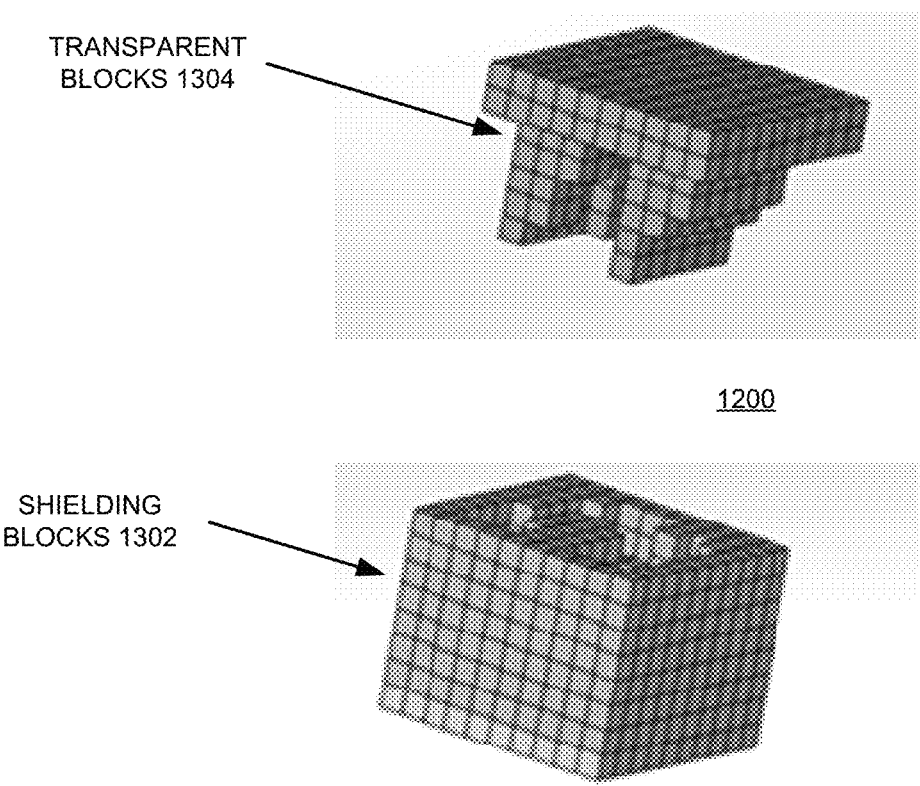
FIG. 13 illustrates an example of a beam modifier like that of FIG. 12 in embodiments according to the invention.

In embodiments, some of the blocks (shielding blocks) in the beam modifier 1200 completely block or attenuate an incident radiation beam and other blocks (transparent blocks) in the beam modifier are transparent to the beam. FIG. 13 illustrates an example of the beam modifier 1200 that includes a combination of shielding blocks 1302 and transparent blocks 1304. In FIG. 13, the shielding blocks 1302 and transparent blocks 1304 are separated. In operation, the transparent blocks 1304 are combined with the shielding blocks to form the beam modifier 1200 in the shape of a cube. That is, the shape formed by the transparent blocks 1304 and the shape formed by the shielding blocks 1302 have complementary surfaces.

In the example of FIG. 13, the shielding blocks 1302 are grouped and the transparent blocks 1304 are grouped, with the transparent blocks located toward the top of the beam modifier 1200. However, the invention is not so limited. For example, shielding blocks and transparent blocks can be intermixed in the beam modifier 1200 in any pattern.

Figure 14:
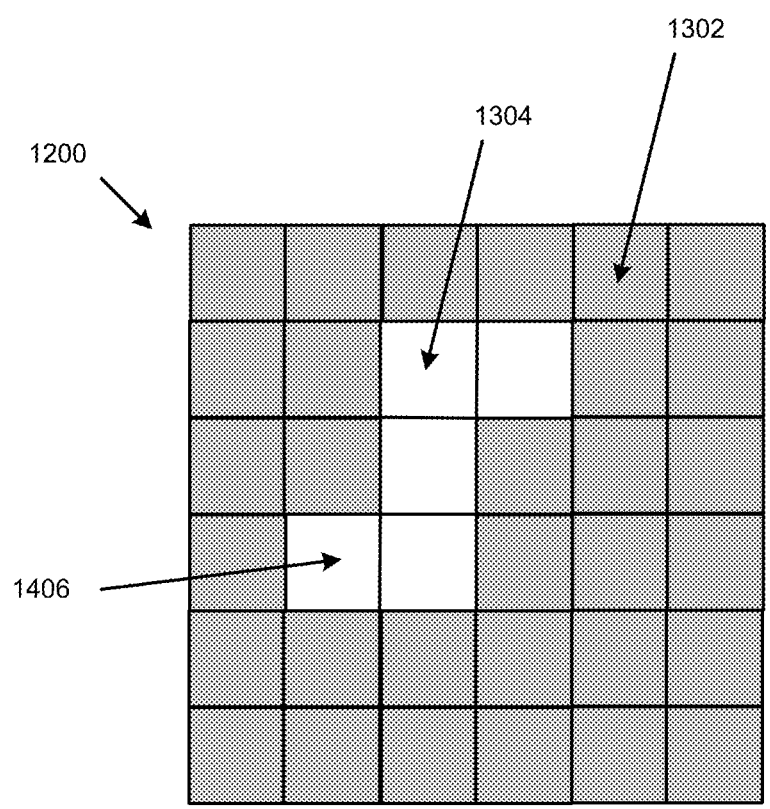
FIG. 14 illustrates a top-down view of a beam modifier like that of FIG. 12 in embodiments according to the invention.

FIG. 14 illustrates a top-down view of the beam modifier 1200 in embodiments according to the invention. Only a single layer (e.g., the top layer) of blocks is shown in FIG. 14. In the example of FIG. 14, the shielding blocks 1302 (which are shaded in the figure) and the transparent blocks 1304 are arranged to shape the equivalent of an opening (transparent portion 1406) in the beam modifier 1200. One or more columns of transparent blocks 1304 extending all the way through the beam modifier 1200 can be formed so that the equivalent of an opening exists all the way through the beam modifier. In operation, an incident radiation beam will pass unimpeded through the transparent portion 1406 (through the transparent blocks 1304) but will be blocked or attenuated by the surrounding shielding blocks 1302.

As mentioned above, there are multiple (e.g., ten) layers of blocks in the beam modifier 1200. Each layer can be configured independently and differently from the other layers. As such, depending on how the blocks in the beam modifier 1200 are configured, the shape of the transparent portion 1406 can be different at each layer of the beam modifier 1200, and the thickness of the shielding material around the transparent portion 1406 can be varied in the z-direction of FIG. 14. Also, more than one transparent portion like the transparent portion 1406 can be readily formed at different locations in the beam modifier 1200. Accordingly, there are many possible arrangements of blocks that can be formed in the path of the beam 101 (FIG. 1), so that each area of the beam can be attenuated or blocked at the same time to achieve a desired dose distribution.

Thus, in operation and depending on how the blocks in the beam modifier 1200 are arranged, some portions of a radiation beam can be blocked by the layers of shielding blocks 1302 and/or some portions of the beam can be attenuated by the shielding blocks, while other portions of the beam are not blocked or attenuated. The amount of attenuation in a portion of the beam depends on the number of overlapping (stacked) shielding blocks that portion of the beam passes through. In this manner, the beam can be shaped by the beam modifier 1200, meaning that the beam modifier both shapes the area of the target covered by the beam and shapes the intensity of the beam that reaches that area, and hence shapes the dose distribution across that area, similar to the example shown previously herein in FIG. 6.

The beam modifier 1200 of FIG. 12 can control the dose distribution of a FLASH shot. After the shot is delivered, the beam modifier 1200 can be rapidly reconfigured by removing some or all of the blocks and then rearranging them for the next shot. This can be quickly achieved using, for example, a programmed robot that can quickly identify, select (e.g., pick up), and position each block under control of the control system 110 (FIG. 1). Alternatively, the beam modifier 1200 can be removed and replaced with another similar type of beam modifier that has already been configured for the next shot. Once the beam modifier is reconfigured or replaced, another shot can be delivered. This process can be repeated until the treatments prescribed by the treatment plan are delivered. Specifically, this process is repeated until the prescribed dose distribution across and through the target is achieved.

The beam modifier 1200 of FIG. 12 can reduce setup time between treatments/shots, which shortens the treatment time and therefore also shortens the total amount of time that the patient needs to remain on the patient support 108 (FIG. 1). The patient does not need to be moved while the beam modifier 1200 is replaced or reconfigured, which improves the repeatability and accuracy of the dosage distribution delivered to the target.

Liquid Shielding-Based Beam Modifier

Figure 15:
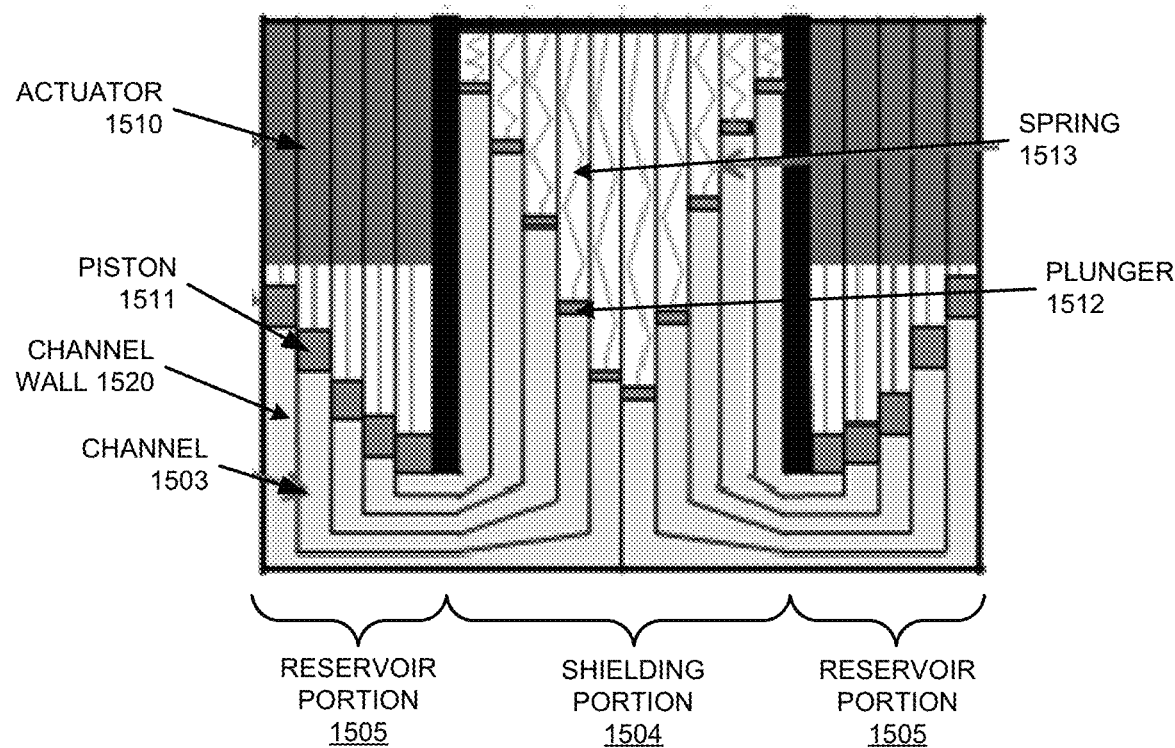
FIG. 15 illustrates a cross-sectional view of a beam modifier in yet other embodiments according to the invention.

FIG. 15 illustrates a cross-sectional view of a beam modifier 1500 in embodiments according to the invention. The beam modifier 1500 is an example of the beam modifier 107 of FIGS. 1 and 2. The beam modifier 1500 includes a number of channels exemplified by the channel 1503. Each channel includes a portion (shielding portion; e.g., portion 1504) that lies within the path of the radiation beam 101 and a portion (reservoir portion; e.g., portion 1505) that lies outside the path of the beam.

In an embodiment, the beam modifier 1500 includes a ten-by-ten arrangement of channels. However, the invention is not so limited.

In the FIG. 15 embodiments, each channel includes an actuator 1510, a piston 1511, a plunger 1512, and a spring 1513. Between the piston 1511 and the plunger 1512, each channel is filled with a heavy liquid or high density liquefied metal (e.g., lead) that is suitable for blocking or attenuating the radiation beam. Each channel includes a channel wall (e.g., the channel wall 1520) that surrounds the channel. In the FIG. 15 embodiments, the channel wall is illustrated as being straight. However, the invention is not so limited.

Figure 16:
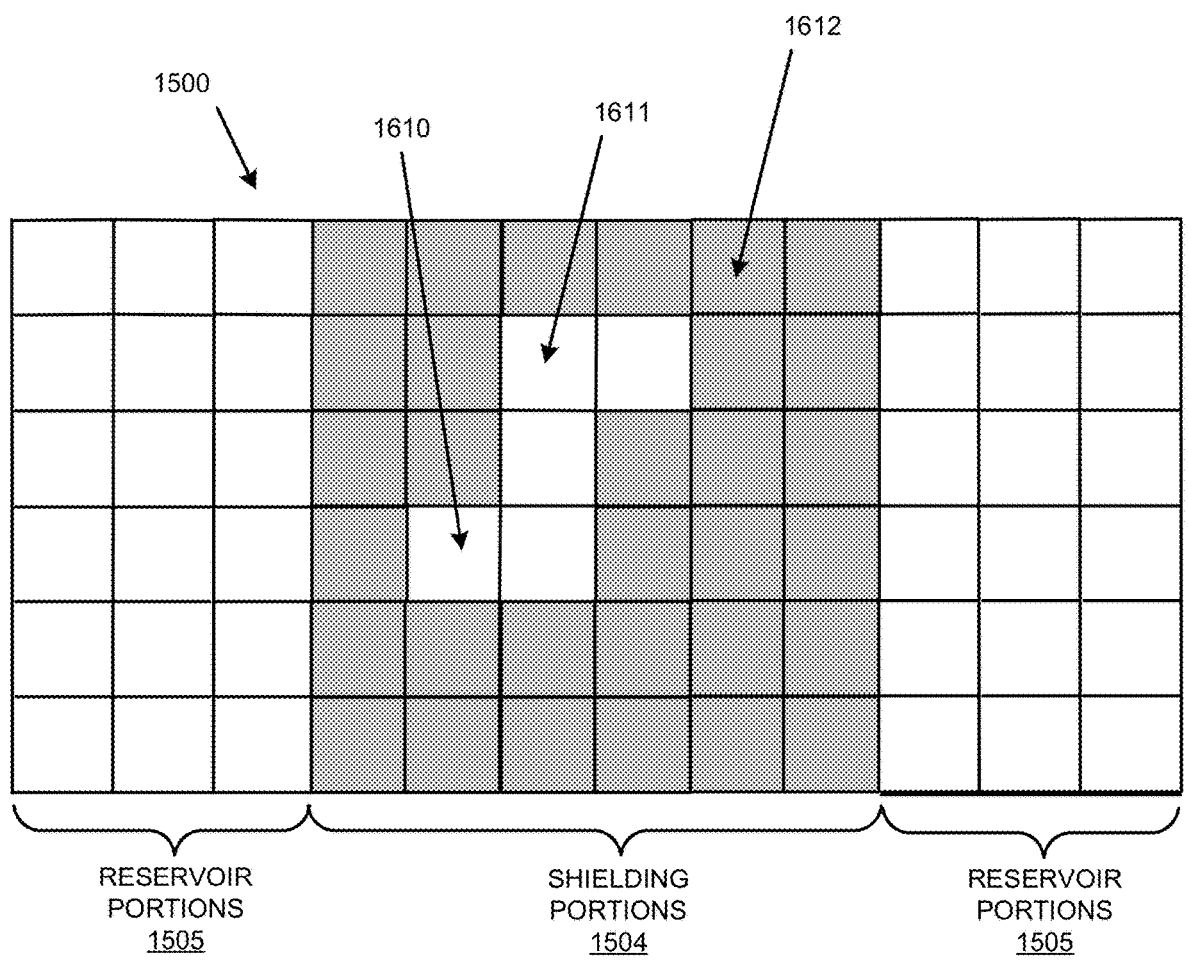
FIG. 16 is a top-down view of a beam modifier like that of FIG. 15 in embodiments according to the invention.

FIG. 16 is a top-down view of the beam modifier 1500 showing the arrangement of the channels in the beam modifier in embodiments according to the invention. In the FIG. 16 embodiments, the channels (e.g., the channel 1503) have a squarish cross-section. However, the invention is not so limited. Also, the channels can have the same cross-sectional areas or they can have different cross-sectional areas. In the FIG. 16 embodiments, the channels are illustrated as being uniformly arranged in rows and columns. However, the invention is not so limited, and the channels can be offset from one another. By offsetting (staggering) the channels, a more uniform dose distribution at the target may be achieved.

With reference again to FIG. 15, the levels of the liquid metal in the channels in the shielding portion 1504 of the beam modifier 1500 can be independently controlled by the control system 110 (FIG. 1). Each channel may include no liquid metal in the shielding portion 1504, or it may be filled to its maximum level with liquid metal, or it may be filled to a level somewhere between the minimum level and the maximum level, independent of the level of liquid metal in the other channels.

To raise the level of liquid metal in, for example, the channel 1503, the actuator 1510 is used to depress the piston 1511, thereby forcing the liquid metal from the reservoir portion 1505 into the shielding portion 1504. This will raise the level of the liquid metal in the shielding portion 1504 of the channel 1503, thereby applying pressure to the plunger 1512 and compressing the spring 1513. To lower the level of liquid metal in the channel 1503, the actuator raises the piston 1511, drawing liquid metal from the shielding portion 1504 of the channel into the reservoir portion 1505 with the aid of pressure applied by the spring 1513 on the plunger 1512.

With reference again to FIG. 16, the equivalent of an opening (transparent portion 1610) in the beam modifier 1500 is formed by channels in the beam modifier that do not include any liquid metal in the shielding portion 1504. In the example of FIG. 16, the channels that are not shaded (e.g., the channel 1611) do not include any liquid metal in the shielding portion 1504, and so those channels form the transparent portion 1610 that extends all the way through the beam modifier 1500. In operation, an incident radiation beam will pass unimpeded through the transparent portion 1610 (through the channel 1611 and the like) but will be blocked or attenuated by the liquid metal in the surrounding channels (the shaded channels, e.g., the channel 1612). The shape of the transparent portion 1610 can be changed by adding liquid metal to one or more of the channels in the beam modifier 1500 and/or removing liquid metal from one or more of the adjacent channels. Also, more than one transparent portion like the transparent portion 1610 can be readily formed at different locations in the beam modifier 1500.

As mentioned above, each channel can be configured independently and differently from the other channels. Accordingly, there are many possible channel configurations that can be formed in the path of the beam 101 (FIG. 1), so that each area of the beam can be attenuated or blocked at the same time to achieve a desired dose distribution.

In operation and depending on how the channels in the beam modifier 1500 of FIG. 15 are arranged (how much liquid metal is contained in the shielding portion 1504 of each channel), some portions of a radiation beam can be blocked and/or some portions of the beam can be attenuated, while other portions of the beam are not blocked or attenuated. The amount of attenuation in a portion of the beam depends on the amount of liquid metal that portion of the beam passes through. In this manner, the beam can be shaped by the beam modifier 1500, meaning that the beam modifier both shapes the area of the target covered by the beam and shapes the intensity of the beam that reaches that area, and hence shapes the dose distribution across that area, similar to the example shown previously herein in FIG. 6.

The beam modifier 1500 can control the dose distribution of a FLASH shot. After the shot is delivered, the beam modifier 1500 can be rapidly reconfigured by changing the level of the liquid metal in any of the channels as needed. In embodiments, the beam modifier 1500 is remotely configured using the control system 110 of FIG. 1. Once the beam modifier 1500 is reconfigured, another shot can be delivered. This process can be repeated until the treatments prescribed by the treatment plan are delivered. Specifically, this process is repeated until the prescribed dose distribution across and through the target is achieved.

The beam modifier 1500 of FIG. 15 can reduce setup time between treatments/shots, which shortens the treatment time and therefore also shortens the total amount of time that the patient needs to remain on the patient support 108 (FIG. 1). The patient does not need to be moved while the beam modifier 1500 is reconfigured, which improves the repeatability and accuracy of the dosage distribution delivered to the target.

Radiation Therapy Method

Figure 17:
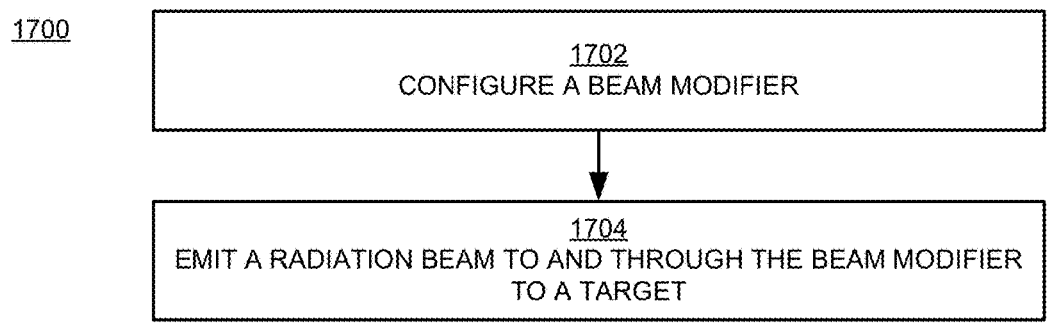
FIG. 17 is a flowchart of a radiation therapy method in embodiments according to the invention.

FIG. 17 is a flowchart 1700 of a radiation therapy method in embodiments according to the invention. Aspects of the operations presented below can be performed using the computing system 1800 of FIG. 18 to implement the control system 110 of FIG. 1.

In block 1702 of FIG. 17, a beam modifier (e.g., the beam modifier 107 of FIG. 1) is configured to intersect an incident radiation beam. In embodiments utilizing the beam modifier 300 of FIG. 3, the configuring is performed by selectively moving rods of the beam modifier to positions that intersect the beam as described above. In embodiments utilizing the beam modifier 1200 of FIG. 12, the configuring is performed by selectively arranging blocks in the beam modifier as described above. In embodiments utilizing the beam modifier 1500 of FIG. 15, the configuring is performed by selectively adding or removing liquid metal from shielding portions of channels as described above.

In block 1704 of FIG. 17, the radiation beam is emitted from a beam emitter into the beam modifier, then to a target.

FIG. 18 shows a block diagram of an example of a computing system 1800 with which the embodiments described herein may be implemented. In its most basic configuration, the system 1800 includes at least one processing unit 1802 and memory 1804. This most basic configuration is illustrated in FIG. 18 by dashed line 1806. The system 1800 may also have additional features and/or functionality. For example, the system 1800 may also include additional storage (removable and/or non-removable) including, but not limited to, magnetic or optical disks or tape. Such additional storage is illustrated in FIG. 18 by removable storage 1808 and non-removable storage 1820. The system 1800 may also contain communications connection(s) 1822 that allow the device to communicate with other devices, e.g., in a networked environment using logical connections to one or more remote computers.

The system 1800 also includes input device(s) 1824 such as keyboard, mouse, pen, voice input device, touch input device, etc. Output device(s) 1826 such as a display device, speakers, printer, etc., are also included.

In the example of FIG. 18, the memory 1804 includes computer-readable instructions, data structures, program modules, and the like. Depending on how it is to be used, the system 1800—by executing the appropriate instructions or the like—can be used as a control system to implement a radiation therapy method. For example, the instructions and the like can be used to remotely configure and reconfigure the beam modifier 107 (FIG. 1) and to remotely trigger the radiation beam 101 (FIG. 1) once the beam modifier is ready.

In summary, embodiments according to the invention provide greater flexibility with respect to patient position, beam delivery system angles, and beam emitter angles, and thus increase the number of treatment options. Embodiments according to the invention also reduce setup times between dose deliveries, thereby shortening the treatment time and therefore also shortening the total amount of time that the patient needs to remain in position while the treatments are completed. Also, the patient does not need to be moved while reconfiguring the beam modifier, which improves the repeatability and accuracy of the dosage distribution delivered to the target.

Significantly, embodiments according to the invention can be used to control dose distribution in FLASH RT, in particular during each single FLASH shot. Even though a shot may last less than a second, the desired dose distribution can be delivered across a target. In general, embodiments according to the invention remove time as a variable when delivering doses to the target.

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

What is claimed is:

1. An apparatus for radiation therapy, the apparatus comprising a plurality of rods comprising:

a first group of opposing rods that are individually moveable parallel to a first axis, wherein the rods in the first group are disposed in a first plurality of layers comprising multiple rods in each layer of the first plurality of layers, and wherein each rod of the multiple rods in each layer of the first plurality of layers is moveable independently of each other; and a second group of opposing rods coupled to the first group and that are individually moveable parallel to a second axis, wherein the first and second axes are not parallel to each other, wherein the rods in the second group are disposed in a second plurality of layers comprising multiple rods in each layer of the second plurality of layers, and wherein each rod of the multiple rods in each layer of the second plurality of layers is moveable independently of each other;

wherein the rods in the first group and the rods in the second group are configured to overlap in an incident radiation beam and shape the radiation beam.

2. The apparatus of claim 1, wherein the rods in the first group comprise:

a first plurality of first rods; and a second plurality of second rods with ends facing ends of the first rods; and wherein the rods in the second group comprise:

a third plurality of third rods; and a fourth plurality of fourth rods with ends facing ends of the third rods.

3. The apparatus of claim 1, wherein each of the rods in the plurality of rods has a cross-sectional shape selected from the group consisting of:

square; rectangular; and hexagonal.

4. The apparatus of claim 1, wherein facing ends of the opposing rods in the first group are complementary in shape, and wherein facing ends of the opposing rods in the second group are complementary in shape.

5. The apparatus of claim 1, wherein the plurality of rods comprises rods that have a portion that is transparent to the radiation beam.

6. The apparatus of claim 1, wherein the plurality of rods comprises rods that completely block the radiation beam.

7. The apparatus of claim 1, wherein the plurality of rods comprises rods that attenuate the radiation beam.

8. The apparatus of claim 1, wherein the first group of rods is collectively moveable about a central point of the first group, and wherein the second group of rods is collectively moveable about a central point of the second group, to change a relative orientation of the first and second axes.

9. The apparatus of claim 1, wherein each rod of the plurality of rods is coupled to a respective drive, wherein each said respective drive comprises a first encoder operable for indicating a position of a respective rod of the plurality of rods, and wherein each said respective rod is adjacent a respective second encoder also operable for indicating the position of said respective rod.

10. A system, comprising:

a control system;

a beam emitter coupled to the control system and operable for emitting a beam of radiation along a beam axis; and a beam modifier coupled to the control system and configured to intersect the beam outside the beam emitter, wherein the beam modifier comprises a plurality of rods configured to intersect the beam from more than two directions, the plurality of rods comprising:
- a first group of rods moveable in directions parallel to a first axis that is orthogonal to the beam axis, and disposed in a first plurality of layers comprising multiple rods in each layer of the first plurality of layers, and wherein each rod of the multiple rods in each layer of the first plurality of layers is moveable independently of each other; and
- a second group of rods that are moveable in directions parallel to a second axis that is orthogonal to the beam axis, disposed in a second plurality of layers comprising multiple rods in each layer of the second plurality of layers, and wherein each rod of the multiple rods in each layer of the second plurality of layers is moveable independently of each other; and configured to overlap rods in the first group in the beam, wherein the first and second axes are not parallel to each other.

11. The system of claim 10, wherein the rods in the first group comprise:
- a first plurality of first rods disposed in a plurality of first overlapping layers, each of the first rods individually moveable in a first direction parallel to the first axis; and
- a second plurality of second rods disposed in a plurality of second overlapping layers, each of the second rods individually moveable in a second direction parallel to the first axis toward the first rods; and wherein the rods in the second group comprise:
- a third plurality of third rods disposed in a plurality of third overlapping layers, each of the third rods individually moveable in a third direction parallel to the second axis; and
- a fourth plurality of fourth rods disposed in a plurality of fourth overlapping layers, each of the fourth rods individually moveable in a fourth direction parallel to the second axis toward the third rods.

12. The system of claim 11, wherein ends of the first rods are complementary in shape to facing ends of the second rods, and wherein ends of the third rods are complementary in shape to facing ends of the fourth rods.

13. The system of claim 10, wherein the first group of rods is collectively moveable about a central point of the first group, and wherein the second group of rods is collectively moveable about a central point of the second group, to change a relative orientation of the first and second axes.

14. The system of claim 10, wherein each of the rods in the plurality of rods has a cross-sectional shape selected from the group consisting of:
square; rectangular; and hexagonal.

15. The system of claim 10, wherein the plurality of rods comprises rods that have a portion that is transparent to the radiation beam.

16. The system of claim 10, wherein the plurality of rods comprises rods that completely block the radiation beam.

17. The system of claim 10, wherein the plurality of rods comprises rods that attenuate the radiation beam.

18. The system of claim 10, wherein each of the rods in the plurality of rods is coupled to a respective drive, wherein each said respective drive comprises a first encoder operable for indicating a position of a respective rod of the plurality of rods, and wherein each said respective rod is adjacent a respective second encoder also operable for indicating the position of said respective rod.

19. A method for radiation therapy, comprising:
- configuring a beam modifier to intersect an incident radiation beam, wherein said configuring comprises selectively moving rods of a plurality of rods to positions to intersect the beam, the plurality of rods comprising first rods that are disposed in a first plurality of layers comprising multiple rods in each layer of the first plurality of layers, and wherein each rod of the multiple rods in each layer of the first plurality of layers is moveable independently of each other and that are moveable in directions that are parallel to a first axis that is orthogonal to the radiation beam, the plurality of rods also comprising second rods that are disposed in a second plurality of layers comprising multiple rods in each layer of the second plurality of layers, and wherein each rod of the multiple rods in each layer of the second plurality of layers is moveable independently of each other and that are moveable in directions that are parallel to a second axis that is orthogonal to the radiation beam, wherein the first rods and the second rods are configured to overlap in the radiation beam, and wherein the first and second axes are not parallel to each other; and
- emitting the radiation beam from a beam emitter into the beam modifier.

20. The method of claim 19, wherein the first rods comprise:
- a first plurality of the first rods disposed in the plurality of first layers; and
- a second plurality of the first rods disposed in the plurality of second layers and with ends facing ends of the first plurality of first rods; and wherein the second rods comprise:
- a first plurality of the second rods disposed in a plurality of third layers; and
- a second plurality of the second rods disposed in a plurality of fourth layers and with ends facing ends of the first plurality of second rods.

* * * * *